(12) United States Patent
Ropp et al.

(10) Patent No.: US 8,399,633 B2
(45) Date of Patent: Mar. 19, 2013

(54) REMOVAL OF LIPOPOLYSACCHARIDES FROM PROTEIN-LIPOPOLYSACCHARIDE COMPLEXES BY NON FLAMMABLE SOLVENTS

(75) Inventors: Philip Alfred Ropp, Chapel Hill, NC (US); Michael Van Alen Murray, Chapel Hill, NC (US)

(73) Assignee: Fujifilm Diosynth Biotechnologies U.S.A., Inc., Morrisville, NC (US)

( * ) Notice: Subject to any disclaimer, the term of this patent is extended or adjusted under 35 U.S.C. 154(b) by 0 days.

(21) Appl. No.: 12/783,319

(22) Filed: May 19, 2010

(65) Prior Publication Data
US 2011/0003976 A1 Jan. 6, 2011

Related U.S. Application Data

(63) Continuation of application No. 10/561,985, filed as application No. PCT/US2004/018992 on Jun. 15, 2004, now abandoned.

(60) Provisional application No. 60/480,899, filed on Jun. 24, 2003, provisional application No. 60/488,596, filed on Jul. 18, 2003.

(51) Int. Cl.
*C07K 1/00* (2006.01)
*C07K 1/06* (2006.01)

(52) U.S. Cl. ........ 530/416; 530/417; 530/412; 530/424; 530/422; 536/127; 435/961

(58) Field of Classification Search ........................ None
See application file for complete search history.

(56) References Cited

U.S. PATENT DOCUMENTS
6,966,992 B2 * 11/2005 Hauser et al. ................. 210/656

OTHER PUBLICATIONS
Petsch et al. J. Biotechnol. 76: 97-119, 2000.*

* cited by examiner

*Primary Examiner* — S. Devi
(74) *Attorney, Agent, or Firm* — Morgan, Lewis & Bockius LLP (57) ABSTRACT

During the production of recombinant proteins from gram negative bacteria, lipopolysaccharides (LPS, endotoxin) are released along with the protein of interest. In many instances, LPS will copurify with the target protein due to specific or non-specific protein-ILPS interactions. We have investigated the ability of alkanediols to effect the separation of LPS from protein-LPS complexes while the complexes are immobilized on anion or cation exchange chromatographic media. Alkanediols provide a safer alternative to the use of other organics such as alcohols or acetonitrile due to their lower toxicity and decreased flammability. In addition, they are less costly than many of the detergents that have been used for such purposes. LPS removal efficiency increased with increasing alkane chain length. 1,2-alkanediols were more effective than terminal alkanediols in the separation of LPS from protein LPS complexes.

15 Claims, 6 Drawing Sheets

REMOVAL OF LIPOPOLYSACCHARIDES FROM PROTEIN-LIPOPOLYSACCHARIDE COMPLEXES BY NON FLAMMABLE SOLVENTS

CROSS-REFERENCE TO RELATED APPLICATIONS

This application is a continuation of U.S. patent application Ser. No. 10/561,985 filed Jan. 13, 2006, now abandoned, which was a national stage application under 35 U.S.C. 371 of International Patent Application No. PCT/US04/18992, filed Jun. 15, 2004, which claims the benefit of priority of U.S. Provisional Application No. 60/480,899 filed Jun. 24, 2003 and U.S. Provisional Application No. 60/488,596 filed Jul. 18, 2003, the disclosures of which are hereby incorporated by reference in their entirety.

FIELD OF THE INVENTION

Embodiments of the present invention generally relate to the removal of lipopolysaccharides (LPS) from protein-lipopolysaccharide complexes.

BACKGROUND OF THE INVENTION

Lipopolysaccharide (LPS) is a major component of the outer membrane of gram negative bacteria. The endotoxic component of LPS is the lipid A portion. It comprises 1,6-linked D-glucosamine residues that are substituted with up to six acyl chains and a core polysaccharide structure to which additional polysaccharide repeating units may be attached. Endotoxin is a potent activator of the innate immune system at low doses while at higher doses endotoxin induces a number of other physical reactions including septic shock and death (Heine et al., 2001). Contamination of therapeutic products with endotoxins is therefore a primary concern for the manufacturers of such products.

Many recombinant proteins are produced in the gram negative bacteria Escherichia coli. The removal of LPS from these recombinant proteins can be a complicated but essential process especially if the proteins are destined for therapeutic uses. Many different processes have been developed for the removal of LPS from proteins based on the unique molecular properties of the endotoxin molecules. These include LPS affinity resins, two-phase extractions, ultrafiltration, hydrophobic interaction chromatography, ion exchange chromatography, and membrane adsorbers (reviewed by Petsch and Anspach, 2000). These procedures have varying degrees of success in the separation of LPS from proteins, which in a large part is dependent on the properties of the protein of interest.

Often, during the production of recombinant proteins, difficulties in the separation of LPS from proteins are encountered due to protein-LPS interactions. For example, and not by way of limitation, in recombinant proteins produced from an E. coli expression system. Several of the published procedures for the separation of LPS from proteins have been investigated, including, but not necessarily limited to, denaturing hydrophobic interaction chromatography (Wilson et al., 2001) and the use of ethanol, isopropanol (Franken et al., 2000), or detergent (Fiske et al., 2001) washes while the protein was immobilized on ion-exchange chromatographic media.

Some experiments have shown that alcohol and detergent washes during ion exchange chromatography are effective in reducing the protein associated LPS levels while poor separation of LPS from the proteins was obtained by the denaturing HIC procedure. The detergents (Zwittergent® 3-12 or 3-14) were shown to be more effective washing agents than the alcohols. Improved LPS clearance was also been achieved while the LPS-protein complexes were bound to a cation exchange resin as opposed to an anion exchange resin but the washing procedures used to remove LPS were effective on both matrices. When the wash procedure is performed on a cation exchanger, once the LPS-protein interactions have been disrupted the LPS should be washed out of the column while the protein is retained. During anion exchange chromatography, the LPS, being negatively charged at most pHs, remains bound to the resin along with the protein. Even though the alcohol and detergent washes were successful at reducing the levels of LPS in the LPS-protein complexes, scaling up and implementing any of these procedures in a manufacturing setting would not be practical. The concentrations of ethanol and isopropanol required to effectively reduce the LPS levels of the LPS binding proteins were greater than 50% (v/v). At these concentrations, these solutions are considered flammable liquids and as such impose many safety and operational restrictions.

The detergents, even though very effective at reducing LPS levels, are relatively expensive and would add significant cost to a manufacturing process and may affect the bioactivity of the protein of interest. Accordingly, Alternative chemicals are desired that could safely and cost effectively be used in place of the alcohols or detergents as washing agents for the separation of LPS from proteins during chromatographic unit operations. Ideally, these chemicals would be relatively inexpensive, well defined chemically, present minimal safety issues, and have minimal impact on the bioactivity of the protein in question when implemented into a process.

SUMMARY OF THE INVENTION

Embodiments of the present invention generally relate to the ability of alkanediols to separate lipopolysaccharides (LPS) or other endotoxins from proteins. In an embodiment, alkanediols are able to effect the separation of LPS from LPS-protein complexes. Accordingly, embodiments of the present invention generally relate to processes using alkanediols to effect to separation of LPS from LPS-protein complexes. In further embodiments, the complexes are immobilized on a resin and the LPS separated therefrom.

DETAILED DESCRIPTION OF THE INVENTION

As used herein, the term "alkanediol" means and refers to a non-aromatic saturated hydrocarbon with the general formula $CnH2n(OH)2$.

As used herein, the terms protein-LPS complex and LPS-protein complex shall be synonymous. The protein-LPS complex may be a loose association, such as, for example and not by way of limitation, by intramolecular forces/intermolecular forces, or binding.

Generally, embodiments of the present invention relate to processes for separating lipopolysaccharides or endotoxins from protein-lipopolysaccharide (or other endotoxin comprising substance) complexes. In an embodiment, a process for separating lipopolysaccharides from protein-lipopolysaccharide complexes comprises the step of washing a protein-LPS complex with an alkanediol containing solution whereby at least a portion of the LPS is removed and/or separated from the protein.

In an embodiment, the LPS-protein complex (or other endotoxin complex) is produced and/or formed during the production of proteins, such as, but not limited to recombinant proteins.

Embodiments of the present invention may use any protein. Various examples include, but are not limited to, Bovine albumin (BSA), bovine holo-transferrin, lactoferrin from bovine milk, lysozyme from chicken egg whites, heat shock proteins, heat shock fusion proteins and the like. The various proteins may be simple or complex, small or large.

Various processes and/or expression systems may be used for the production of recombinant proteins. Any expression system may be used for the production of recombinant proteins. In an embodiment, the expression system is bacterial. In such embodiments, gram negative bacterial expression systems may be used, such as an *E. coli* expression system. However, other types of bacterial systems may also be used, for example, and not by way of limitation, *Caulobacter crescent* and *Proteus mirabilis*.

In general, any system comprising endotoxin(s) can use embodiments of the present invention to separate the endotoxin from the protein. For example, in an embodiment endotoxin(s) are an impurity in a system comprising proteins. It is well known in the art that endotoxin(s) can, in some instances, be found as contaminants in raw materials or during processing. Such endotoxins can be removed and/or separated by various embodiments of the present invention.

Any alkanediol may be used with various embodiments of the present invention. Suitable, non-limiting examples include, 1,5-pentanedial, 1,6-hexanediol, 1,2-hexanediol, 1,2-butanediol, 1,4-butanediol, and 1,7-heptanediol. In an embodiment, alkanediols of the present invention are long chain alkanediols.

Alkanediols provide increased safety over the commonly used eluents, like acetonitrile, ethanol, and methanol, since the alkanediols are all nonflammable compounds. Further, alkanediols are soluble in water and they are not cost prohibitive for a large number of processes.

In other embodiments, various processes are utilized to assist and/or facilitate separation of the protein-LPS complex. In various examples of these embodiments, the protein-LPS complex is attached to a substrate. Various methods of attachment include retaining, attracting, binding, applying, immobilizing and/or removably affixing to a substrate. Either the protein or the LPS may be attached. In an embodiment, the LPS-protein complex is bound or immobilized on a resin. Suitable resin types include, but are not limited to affinity resins, anion exchange resins, cation exchange resins, and the like, such as a SP Sepharose® Fast Flow resin (SPSFF resin). However, the choice of resins is a matter of routine skill in the art and can be made to serve the particular needs of the process.

In an embodiment, the LPS-protein complex is bound to an ion exchange resin under conditions such that the protein binds to the resin of the column. An alkanediol wash solution is then applied to the column whereby at least a portion of the LPS is separated from the LPS-protein complex and elutes with or about the alkanediol. In an embodiment, greater than 50% of the LPS is separated from the LPS-protein complex. In an alternate embodiment, greater than 75% of the LPS is separated from the LPS-protein complex. In another embodiment, greater than 80% of the LPS is separated from the LPS-protein complex. In yet another embodiment, greater than 85% of the LPS is separated from the LPS-protein complex. In an alternate embodiment, greater than 90% of the LPS is separated from the LPS-protein complex.

In another embodiment, greater than 95% of the LPS is separated from the LPS-protein complex. In another embodiment greater than 97% of the LPS is separated from the LPS protein complex. In another embodiment, greater than 99% of the LPS is separated from the LPS-protein complex. In another embodiment, greater than 99.9% of the LPS is separated from the LPS-protein complex.

In an embodiment, after separation and/or removal of the LPS, the protein can be eluted from the resin. The protein may eluted by means common in the art and as appropriate for the resin. In an example, for ion exchangers changes in pH and/or increased conductivity can be used to elute the protein.

In an embodiment, 50% of the protein eluted from the resin is free of LPS or other endotoxin. In an alternate embodiment, 75% of the protein eluted from the resin is free of LPS or other endotoxin. In an alternate embodiment, 80% of the protein eluted from the resin is free of LPS or other endotoxin. In an alternate embodiment, 85% of the protein eluted from the resin is free of LPS or other endotoxin. In an alternate embodiment, 90% of the protein eluted from the resin is free of LPS or other endotoxin. In an alternate embodiment, 95% of the protein eluted from the resin is free of LPS or other endotoxin. In an alternate embodiment, 97% of the protein eluted from the resin is free of LPS or other endotoxin. In an alternate embodiment, 99% of the protein eluted from the resin is free of LPS or other endotoxin. In an alternate embodiment, 99.9% of the protein eluted from the resin is free of LPS or other endotoxin.

In various embodiments, another wash is utilized to remove/separate the protein from the resin. In an alternate embodiment, the protein elutes without a wash, such that the resin only slowed the protein elution, thereby separating the LPS from the protein. The degree of separation can be varied depending upon the resin used. Likewise, a resin can be constructed to change the elution profile of the LPS-protein complex such that the LPS or protein component elutes at a different time than the other component.

Accordingly, various embodiments of the present invention comprise processes such as:

A process for removing an endotoxin from recombinantly produced proteins comprising a Lipopolysaccharide (LPS)-protein complex comprising the steps of:

immobilizing the complex to an ion exchange resin;

washing the resin with an alkanediol whereby at least a portion of the LPS is separated from the complex; and, eluting at least a portion of the protein from the resin.

In alternate embodiments, the LPS is affixed to the resin and the protein is first eluted.

In further embodiments, the present invention comprises a process for disrupting a lipopolysaccharide (LPS)-protein complex comprising washing the complex with an alkanediol.

In yet further embodiments, the present invention comprises processes for increasing the retention time of a protein on a resin comprising the step of washing the resin with an alkanediol. In an example of such an embodiment, after a wash with a hexanediol, such as 1,2-hexanediol, to remove the LPS, increasing the salt concentration on the resin fails to elute the protein. Such embodiments are useful for high salt environments and where one may wish to alter the selectivity of the resin for proteins.

Accordingly, embodiments of the present invention further comprise methods of separating LPS from a protein-LPS complex in a high salt, conductivity, environment comprising the steps of:

immobilizing the complex to an ion exchange resin;

washing the resin with 1,2-hexanediol whereby at least a portion of the LPS is separated from the complex; and, eluting at least a portion of the protein from the resin by modifying the pH. In preferred embodiments of this type, the concentration of alkanediol is greater than about 5%. However, any concentration may be used.

While the invention has been described in connection with specific embodiments thereof, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended Claims are intended to cover such differences. Furthermore, all patents mentioned herein are hereby incorporated by reference.

For a further understanding of various embodiments of the present invention, reference should be had to the following examples:

EXAMPLES AND EXPERIMENTS

Materials

Bovine albumin (BSA), bovine holo-transferrin, lactoferrin from bovine milk, lysozyme from chicken egg whites, lipopolysaccharides from *Escherichia coli* serotype O55:B5, and BSTFA were purchased from Sigma Chemical Co. (St. Louis, Mo.). Acetic acid, Tris (base), sodium hydroxide (NaOH), hydrochloric acid, sodium chloride (NaCl), ethanol, isopropanol, sodium dodecyl sulfate (SDS), and sodium phosphate dibasic 7-hydrate were purchased from J. T. Baker Chemical Co. (Phillipsburg, N.J.). 1,6-Hexanediol was from BASF Co. (Mount Olive, N.J.). 1,2-Hexanediol, 1,2-butanediol, and Zwittergent® 3-14 (Zw 3-14) were purchased from Fluka (Milwaukee, Wis.). 1,4-Butanediol and ethylene glycol were purchased from Aldrich (Milwaukee, Wis.). Phosphate buffered saline (PBS), 10×, was purchased from Bio-Rad Laboratories, Inc. (Hercules, Calif.). *Escherichia coli* BODIPY® FL conjugate lipopolysaccharide, serotype O55:B5, (BODIPY®-LPS) and EnzChek® Lysozyme Assay Kit were purchased from Molecular Probes, Inc. (Eugene, Oreg.). Pyrosol, *Limulus Amebocyte* Lysate (LAL) Pyrotell-T®, LAL reagent water (LRW), and control standard endotoxin from *E. coli* O113:H10 (CSE), were obtained from Associates of Cape Cod, Inc. (Falmouth, Mass.). SP Sepharose® fast flow (SPFF) resin, Q Sepharose® fast flow (QFF) resin, and HR 10/10 columns were from Amersham Biosciences (Piscataway, N.J.). Clear polystyrene 96-well microtiter plates were from Associates of Cape Cod, Inc. (Falmouth, Mass.) and black 96-well microtiter plates from NUNC (Rochester, N.Y.). β-Hydroxytetradecanoic acid, β-hydroxytridecanoic acid, β-hydroxyundecanoic acid, β-hydroxytridecanoate, β-hydroxytetradecanoate, and β-hydroxyandecanoate were purchased from Matreya, Inc. (Pleasant Gap, Pa.). Heptane was purchased from Spectrum (New Brunswick, N.J.).

Methods

Viscosity Measurements

A Brookfield Model 1 LVT Viscometer equipped with a ULA-Y adapter (Middleboro, Mass.) was used for viscosity determinations. All measurements were performed at 20° C.

LPS-Protein Complex Formation

Protein stock solutions were prepared in the column equilibration buffers to a final concentration of 10 to 11 mg/ml. LPS O55:B5 stock solution was prepared in Milli-Q® water and BODIPY®-LPS stock solution was prepared in PBS or column equilibration buffers to a final concentration of 1 mg/ml. This is approximately 100 µM final concentration based on a molecular weight of O55:B5 LPS of 10,000 Da.

The LPS-protein complexes were formed by adding to a polypropylene tube 1 part LPS solution to 9 parts protein solution, v/v. The tube was vortexed, wrapped in aluminum foil, and then incubated at room temperature for 16 to 72 hours for BSA and transferrin or incubated at 37° C. for at least 4 hours for lactoferrin.

LAL and BODIPY® Analysis

A SpectraMax® Gemini XS microplate spectrofluorometer from Molecular Devices Co. (Sunnyvale, Calif) was used for the BODIPY®-LPS fluorescent microplate assay and a SpectraMax® 190 microplate spectrophotometer (Molecular Devices) for the LAL kinetic turbidimetric assay (KTA). Reference materials were analyzed in triplicate and samples either in duplicate or triplicate. The results were plotted and analyzed using SOFTmax PRO® software version 3.1.1 (Molecular Devices).

A. BODIPY®-LPS Assay

Three fold serial dilutions of the BODIPY®-LPS stock solution were prepared from 0.81 to 0.03 µM. The analytical procedure of the BODIPY®-LPS assay was a modification of the assay used by Yu and Wright (1996) as follows. To each well of a black microtiter plate 20 µl of 15% SDS, prepared in Milli-Q® water, followed by 180 µl sample or standard were added. The plate was shaken for 10 seconds at 37° C. and read immediately in fluorescence mode. The optimal excitation (490 nm), emission (525 nm), and cutoff wavelengths (515 nm) were determined for the BODIPY®-LPS. The assay for BODIPY®-LPS demonstrated a linear range from 0.03 to 0.81 µl (54 to 1458 ng) with a limit of detection of/LOQ values less than 0.01 µl (18 ng) and a limit of quantification of 0.03 µM (54 ng).

B. LAL Kinetic Turbidimetric Assay (KTA)

Samples were adjusted to a pH between 6 and 8 with Pyrosol, if needed. CSE and Pyrotell-T® were reconstituted with LRW. The linear curve of CSE was from 0.03 to 1.00 EU/ml. The analytical procedure of LAL KTA was as follows. To each well of a clear polystyrene microtiter plate 100 µl of sample or standard and 100 µl of Pyrotell-T® were added. For spiked samples, 5 µl of 2.00 EU/ml CSE was added to obtain 0.10 EU/ml CSE level. The plate was shaken for 10 seconds and data collected, every minute, in the kinetic mode at 405 nm for 1 hour at 37° C.

C. LPS Analysis by Gas Chromatography

Quantitative analysis for the relative level of LPS present in samples by gas chromatography mass spec (GCMS) was based on the method by Mielniczul et al. (1992) and utilized a 6890 gas chromatograph with a 5973 mass selective detector from Agilent (Foster City, Calif.). The column used was a DB-5MS column (30 cm×0.25 mm i.d.×0.25 µm film thickness) from J&W Scientific (Foster City, Calif.). The linear curve for surrogate and target compounds ranged from 1.6 to 100 pg/µl and the internal standard was kept constant at 50 pg/µl. Briefly, the method of sample preparation and GCMS analysis were as follows. Samples and a known amount of surrogate, β-hydroxytridecanoic acid, were added to 5 ml glass reaction vials. Aqueous samples were hydrolyzed in 6 N HCl at 90 to 100° C. overnight to liberate β-hydroxytetradecanoic acid from LPS. The fatty acids were extracted twice from the hydrolysate with heptane and then dried under nitrogen. The fatty acids were methylated by incubation at 80 to 90° C. in 3 N methanolic HCl for 30 minutes. Water was added to quench the reaction and then the methyl esters extracted twice with heptane. The methyl esters were then dried under nitrogen. The methyl esters were derivatized by adding BSTFA/pyridine (2:1, v/v) and incubating at 80 to 90° C. for 15 to 20 minutes before undergoing the final drying step under nitrogen. Samples were reconstituted with a 50 pg/µl internal standard, methyl-3-trimethylsilyl-undecananoic acid, prepared in heptane. Standards and samples were injected in splitless mode and at 1 µl injection volume. Initial oven temperature was held at 90° C. for 4 minutes and then ramped at 20° C. per minute to 250° C. followed by a 10° C. per minute ramp to 300° C. The mass spectrometer was set for an EM offset voltage of 500 and the solvent delay at 5.2 minutes. Selective ion monitoring was used to monitor methyl-3-TMS-undecanoate at ions 175 and 273, methyl-3-TMS-tridecanoate at 11.0 minutes and ions 175 and 301, and methyl-3-TMS-tetradecanoate at 11.7 minutes and ions 175 and 315. Chromatograms were reported using Chemstation® for MSD Productivity software.

Lysozyme Assay

Lysozyme activity was determined using the EnzChek® Lysozyme Assay Kit according to the manufacturers instructions.

Chromatography

All chromatography was performed on ÄKTA® explorer 100 FPLC systems (Amersham Biosciences) equipped with a gradient pump (P-900), a 500 µl or 2000 µl injection loop, a variable wavelength detector (UV-900), and a pH and conductivity monitor (pH/C-900). All chromatographic experiments were performed at a flow rate of 200 to 300 cm/hr at ambient temperature. During the alkanediol washes the flow rate was dropped to 150 to 200 cm/hr to minimize the increase in system back pressure due to the increased viscosity of the alkanediol solutions. Chromatograms were reported using Unicorn software version 3.21 or 4.0. The resins were packed in 1 cm diameter columns to bed heights of 7 to 11 cm. The ÄKTAs® and columns were sanitized either with 0.5 N NaOH for 60 to 120 minutes or 0.1N NaOH for greater than 16 hours before each chromatographic run. The column and ÄKTAs® were then rinsed with Milli-Q® water just prior to system equilibration with the appropriate buffers.

Alkanediols, ethanol, and isopropanol were prepared as v/v solutions with the same chemical compositions and pH as the equilibration buffers, while 1,6-hexanediol and Zwittergent® 3-14 were prepared as w/v solutions.

D. Cation Exchange Chromatography

For transferrin, a SP Sepharose® Fast Flow column was charged with 100 mM Acetate, 1 M NaCl, pH 5, and equilibrated with 100 mM Acetate, pH 5. After loading, the resin was washed with the equilibration buffer and then eluted with 50 mM sodium phosphate, 1 M NaCl, pH 7.5. When an organic or detergent wash was performed, it was applied after the initial wash step and was for 6 CV unless otherwise stated. This wash was followed by a second wash with equilibration buffer to remove the organic or detergent prior to elution.

The chromatography for BSA was identical to that of transferrin except that the pH of all chromatography buffers was 4.5. When 1,2-hexanediol was used as the washing agent, the eluent was changed to 50 mM sodium phosphate, 1 M NaCl, pH 7.5.

Lactoferrin chromatography was similar to transferrin except that the resin was charged with 1 M sodium chloride, 20 rnM sodium phosphate, pH 7.5, equilibrated in 20 mM sodium phosphate, pH 7.5, and eluted with 1 M sodium chloride, 20 mM sodium phosphate, pH 7.5. The chromatography for lysozyme was similar to that for transferrin except that the resin was charged with 1 M NaCl, 20 mM Tris, pH 8.0, equilibrated in 50 mM Tris, pH 8.0 and eluted with 1 M NaCl, 20 mM Tris, pH 8.0.

E. Anion Exchange Chromatography

For BSA, a Q Sepharose® Fast Flow column was charged with 50 mM Tris, 1 M NaCl, pH 8.0 and equilibrated with 50 mM Tris, pH 8.0. After loading, the resin was washed with equilibration buffer. BSA was eluted with 25 mM Acetate, pH 4.5, and LPS with 25 mM Acetate, 1 M NaCl, pH 4.5. When an alkanediol wash was performed, it was inserted after the initial wash step and was for 6 CV. This wash was followed by a second wash with equilibration buffer to remove the alkanediol.

Results and Discussion

Table I summarizes the molecular weights and isoelectric points of the proteins used in this study. BSA, transferrin, and lactoferrin have all been shown to bind LPS (Dzarski, 1994; Berger and Beger, 1987; and Appelmelk et al., 1994). Lysozyme was used to assess the effects of the washing agents on enzyme activity.

TABLE I

Molecular Weights and Isoelectric Points of Proteins Used in this Study

| Protein | Molecular Weights | pI |
|---|---|---|
| Albumin, bovine fatty acid free low endotoxin | 66400 | 5.56 |
| Transferrin, bovine holo | 74800 | 6.5 |
| Lactoferrin, bovine | 75200 | 8.52 |
| Lysozyme, chicken egg white | 14300 | 9.65 |

Table II summarizes some of the physical properties of the alkanediols used in this study. Also included are ethanol and isopropanol, which have been used for LPS removal in other processes (Franken et al., 2000), for comparison.

TABLE II

Physical Properties of Alkanediols Used in this Study

| Compound | [2]Boiling Point (° C.) | [1]Melting Point (° C.) | [1]Flash Point (° C.) | [2]Explosion limits, air Lower | [2]Explosion limits, air Upper | [2]Autoignition (° C.) |
|---|---|---|---|---|---|---|
| 1,2-hexanediol | 223 | NA | 122 | NA | NA | 390 |
| 1,6-haxanediol | 250 | 45 | 147 | 6.6% | 16% | 319 |
| 1,5-pentanediol | 242 | −16 | 129 | 1.4% | 13.2% | NA |
| 1,2-butanediol | 194 | −50 | 93 | 2.4% | 13.5% | 390 |
| 1,4-butanediol | 230 | 16 | 121 | 1.95% | 18.3% | 420 |
| 1,3-propanediol | 214 | −27 | 131 | NA | NA | 400 |
| 1,2-ethanediol | 195 | −13 | 111 | 3.2% | 15.3% | 400 |
| Ethanol | 78.3 | −114.1 | 12 | 3.3% | 19% | 363 |
| Isopropanol | 82.4 | 88.5 | 12 | 2.5% | 12% | 460 |

[1]data obtained from CabridgeSoft Corp. at Chemfinder.com
[2]data from Material Data Safety Sheets
NA, not available SP Sepharose® Fast Flow Chromatography of LPS and LPS-Protein Complexes The LPS elution profiles of LPS by itself and LPS-BSA complexes on SP Sepharose® Fast Flow resin were determined by LAL-KTA analysis of selected column fractions (Table III). When LPS was chromatographed by itself the LPS was detected primarily in the wash-unbound fraction as expected. Chromatography of the LPS-BSA complexes resulted in the majority of the LPS being detected in the BSA eluate fraction confirming the LPS binding property of BSA (Dziarski, 1994) and demonstrating that the BSA-LPS complexes are stable under cation exchange chromatography conditions employed.

TABLE III

SPFF Chromatography Elution Profiles of LPS and LPS-BSA
LPS and LPS-BSA complex were chromatographed on SP Sepharose Fast Flow. Column fractions were analyzed for LPS by LAL KTA as described in the methods.

| | BODIPY-LPS (% Recovery) | | |
|---|---|---|---|
| Sample | Load | Wash-unbound | Elution |
| BODIPY-LPS | 100 | 82 | 5 |
| BODIPY-LPS- BSA Complex | 100 | 3 | 90 |

The LAL KTA is a laborious and costly assay to use to determine the distribution of LPS in the column fractions. A fluorescent based assay for LPS was developed to monitor the to column fractions. This assay used fluorescently tagged LPS, BODIPY®-LPS, in place of the non-labeled LPS, which allows for the quick analysis of the column eluates by fluorescence spectroscopy. The fluorescence of the BODIPY® maker in the BODIPY®-LPS conjugate has been shown to be quenched when the LPS is complexed with itself or protein. Addition of SDS to the sample disrupts the LPS-LPS or LPS-protein complexes and results in an increase in fluorescence (Yu and Wright, 1996). The assay was developed as a microtiter plate based assay that allowed for the quick and quantitative analysis of BODIPY®-LPS in the chromatography fractions.

Figure 1A:
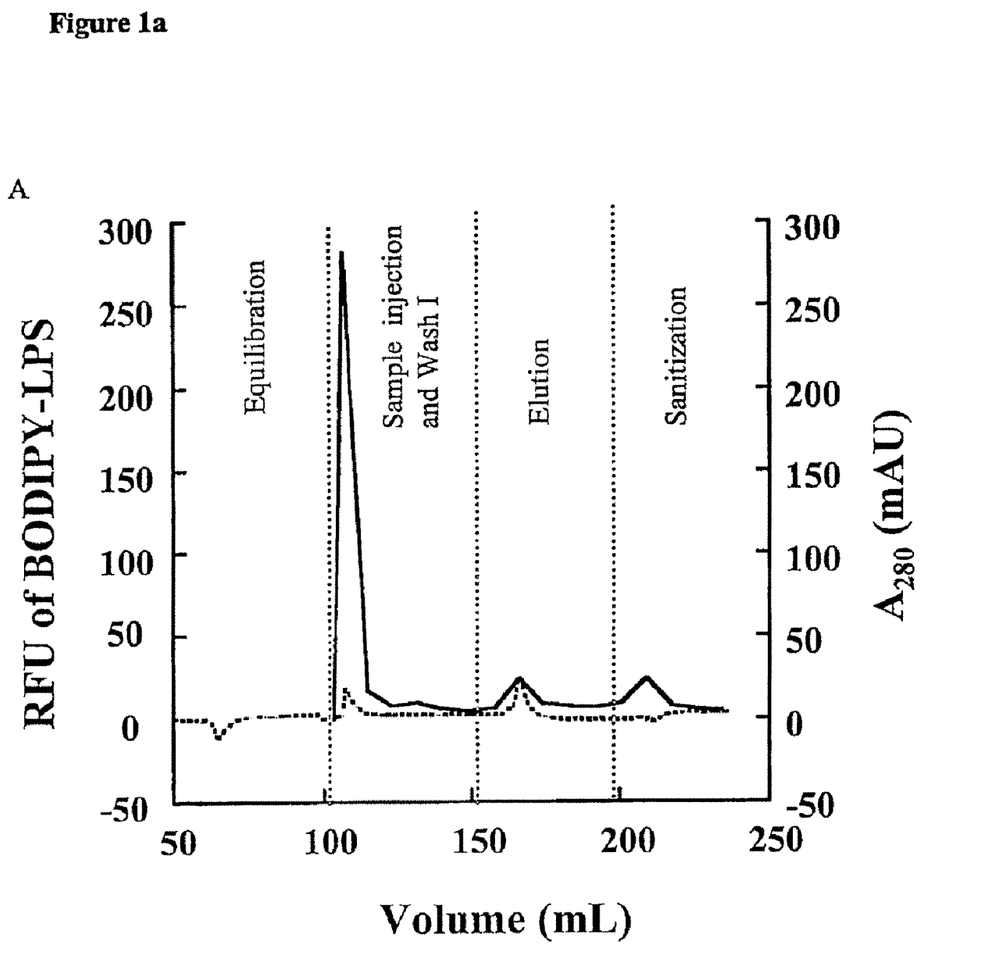
FIG. 1a is an illustration of the SP Sepharose® Fast Flow Elution Profile of BODIPY®-LPS. The dotted line is UV signal at 280 nm and the solid line corresponds to BODIPY® fluorescence expressed in relative fluorescence units (RFU).
Figure 1B:
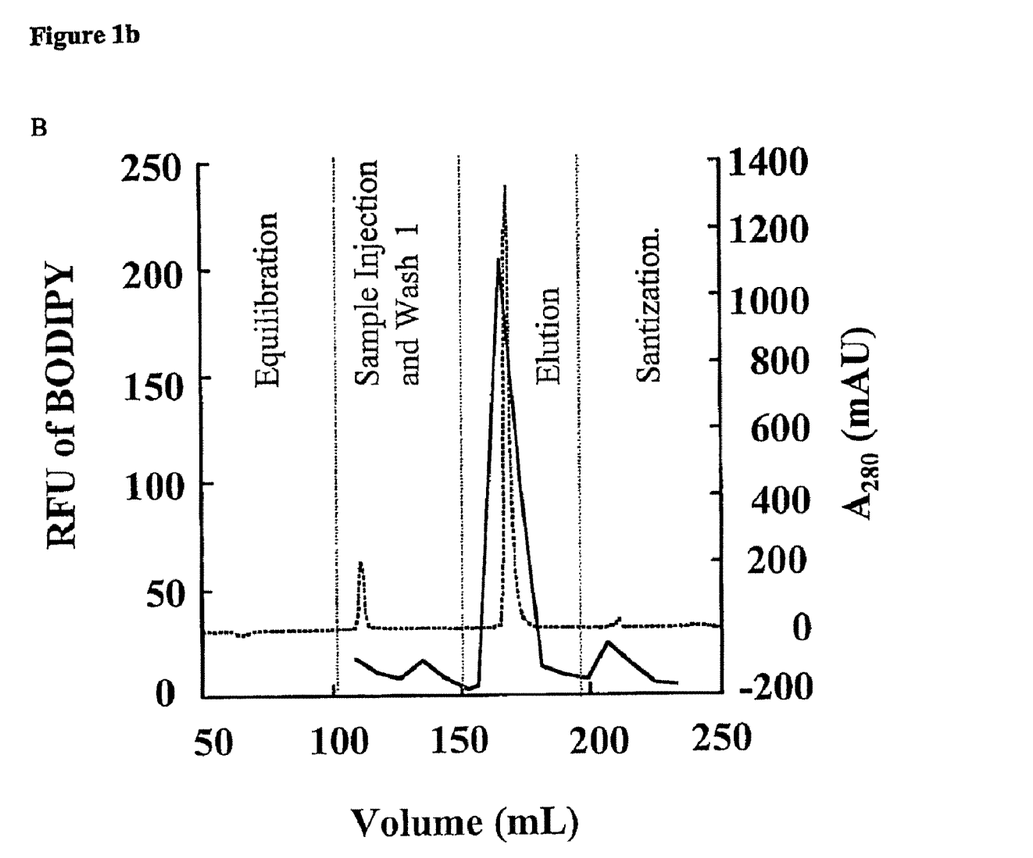
FIG. 1b is an illustration of the SP Sepharose® Fast Flow Elution Profile of BODIPY®-LPS-Transferrin Complex. The dotted line is UV signal at 280 nm and the solid line corresponds to BODIPY® fluorescence expressed in relative fluorescence units (RFU).

To determine if the BODIPY® marker interfered with BSA-LPS complex formation or behaved differently during cation exchange chromatography the preceding analysis was repeated using BODIPY®-LPS and BODIPY®-LPS-protein complexes. The elution profiles of BODIPY®-LPS and BODIPY®-LPS-protein complexes were similar (Table IV) to the elution profiles of LPS and LPS-BSA above. This demonstrates that the BODIPY® marker does not interfere with the ability of BSA or transferrin to bind LPS and that the BODIPY® group does not alter the chromatographic profile of the LPS. FIG. 1 shows typical SP Sepharose® Fast Flow profiles for BODIPY®-LPS (A) and the BODIPY®-LPS-transferrin complex (B).

TABLE IV

SPFF Chromatography Elution Profiles of
BODIPY-LPS and BODIPY-LPS-Protein
BODIPY-LPS and BODIPY-LPS-Protein complex
were chromatographed on SP Sepharose Fast Flow.
Column fractions were analyzed for
BODIPY-LPS by the BODIPY
assay as described in the methods.

| | BODIPY-LPS (% Recovery) | | |
|---|---|---|---|
| Sample | Load | Wash-unbound | Elution |
| BODIPY- LPS | 100 | 82 | 5 |
| BODIPY-LPS-BSA Complex | 100 | 2 | 90 |
| BODIPY-LPS-Transferrin Complex | 100 | 6 | 74 |

Reduction of LPS from LPS-Protein Complexes by Alkanediols During SP Sepharose® Fast Flow Chromatography Initial experiments examined the capability of a 50% 1,6-hexanediol wash step to reduce the amount of BODIPY®-LPS complexed with BSA during cation exchange chromatography. A 3 column volume (CV) wash with 1,6-hexanediol lowered the amount of BODIPY®-LPS complexed with BSA by about 21%. Increasing the length of the 1,6-hexanediol wash step from 3 CV to 6 CV improved the removal of BODIPY®-LPS from the BSA complex to about 49%. While an additional 3 CV increase in the 1,6-hexanediol wash step to 9 CV provided improvement (51%) in BODIPY®-LPS removal. All additional experiments were carried out with a 6 CV alkanediol wash step.

Figure 2:
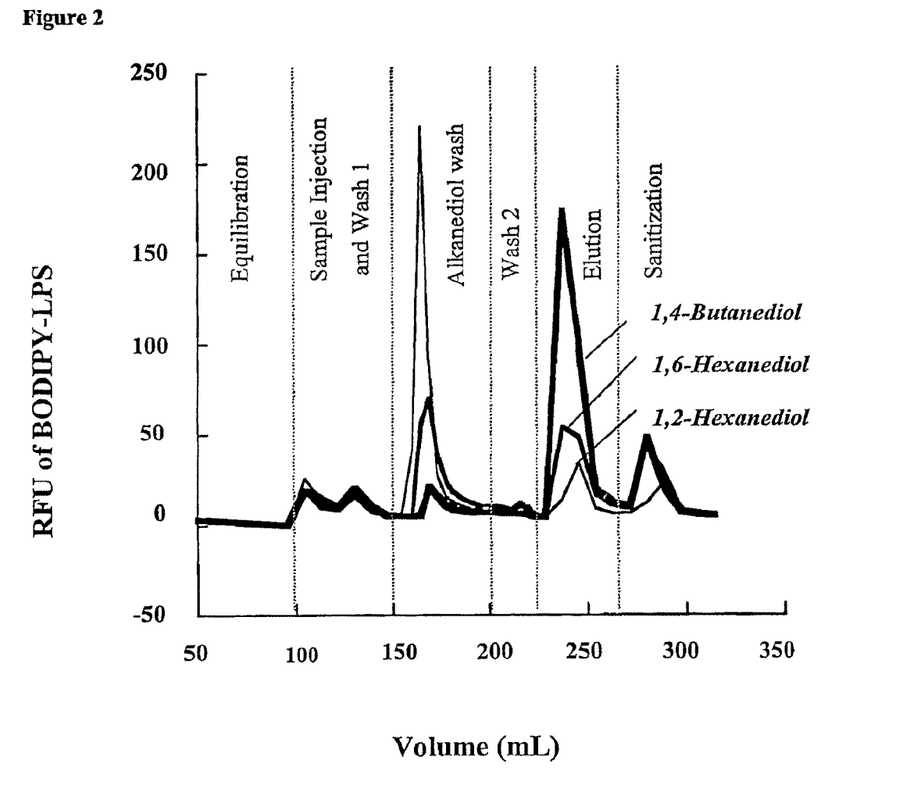
FIG. 2 is an illustration of BODIPY®-LPS Elution Profiles of BODIPY®-LPS-Transferrin Complexes on SP Sepharose® Fast Flow in Conjunction with Alkanediol Washes. BODIPY®-LPS-transferrin complexes were generated, loaded onto a SP Sepharose® Fast Flow column and the column washed with 50% solutions of 1,4-butanediol, 1,6-hexanediol, or 1,2-hexanediol.
Figure 3:
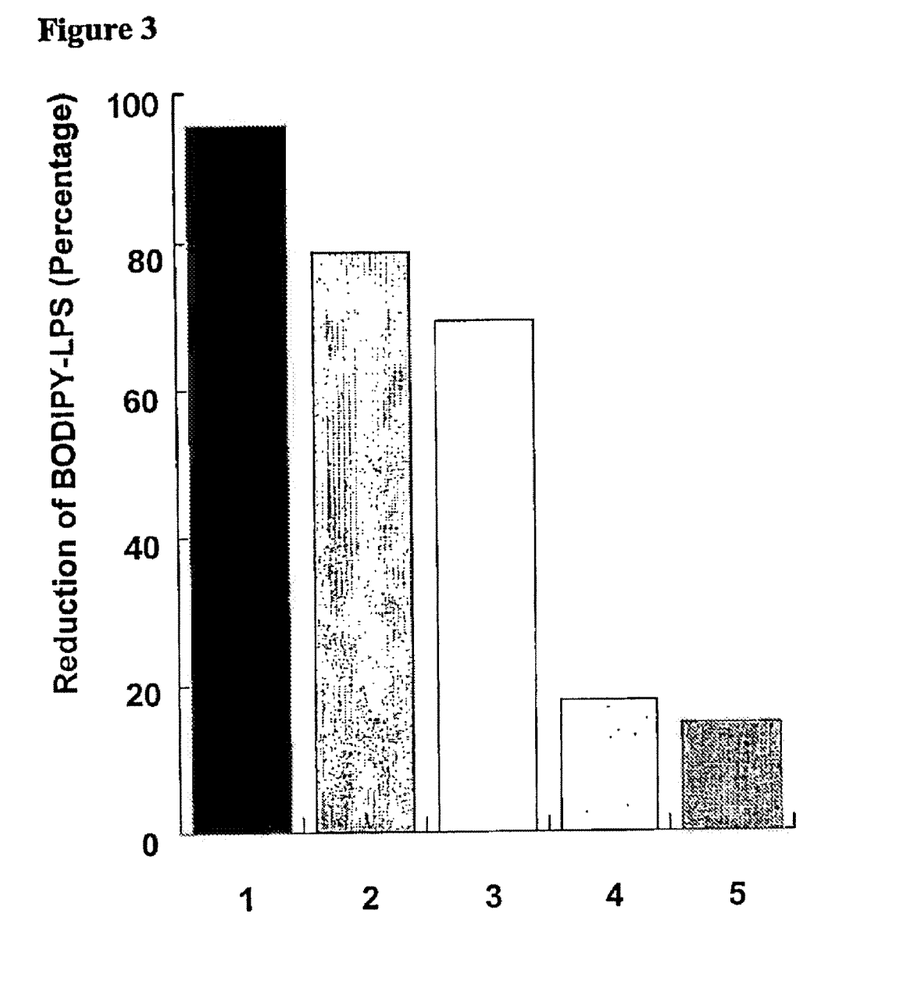
FIG. 3 is an illustration of the reduction of BODIPY®-LPS from BODIPY®-LPS-Transferrin Complexes in SP Sepharose® Fast Flow Eluates by Alkanediols. Zero percent reduction corresponds to a control run without an alkanediol wash. 1,1,2-hexanediol; 2, 1% Zwittergent® 3-14; 3,1,6-hexanediol; 4, ethylene glycol; and 5,1,4-butanediol.
Figure 4:
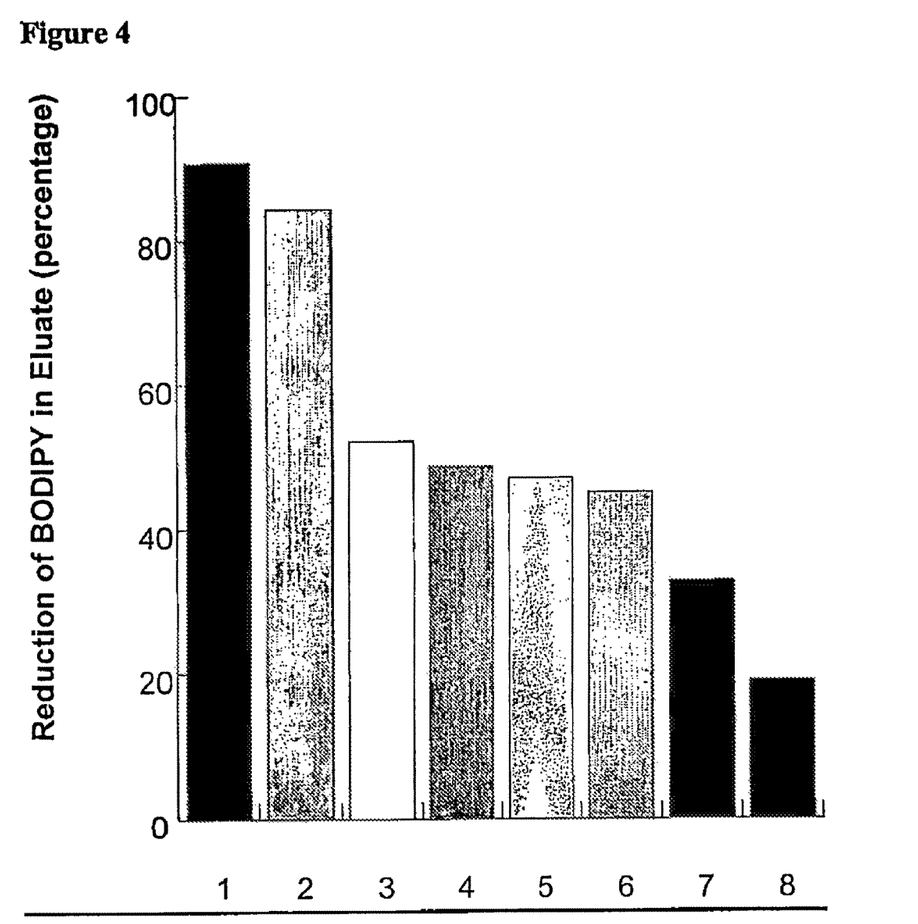
FIG. 4 is an illustration of the reduction of BODIPY®-LPS from BODIPY®-LPS-BSA complexes in SP SEPHAROSE® Fast Flow eluates by Alkanediols. Zero percent reduction corresponds to a control run without an alkanediol wash. 1,1,2-hexanediol; 2, 1% Zwittergent® 3-14; 3,1,2-butanediol; 4,1,6-hexanediol; 5, 50% isopropanol; 6, 75% ethanol; 7,1,4-butanediol; and 8, ethylene glycol.

The effectiveness of a series of alkanediols to remove LPS from proteins while the proteins were bound to ionic solid supports were compared to those of ethanol, isopropanol, and Zwittergent® 3-14, which had been shown to be effective in removing LPS from a LPS binding protein. A SP Sepharose® Fast Flow column was loaded with BODIPY®-LPS-transferrin complex. The resin was washed with six column volumes of a 50% alkanediol solution and then eluted. Fractions were collected and assayed for BODIPY®-LPS (FIG. 2). As the chain length of the alkanediol was increased from four to six carbons, the fluorescence of the alkanediol wash fractions increased while the fluorescence of the eluate fractions decreased. This demonstrated that alkanediols removed BODIPY®-LPS from the transferrin complex. FIGS. 3 and 4 illustrate the effects of alkanediol structure on BODIPY®-LPS removal from transferrin and BSA, respectively. BODIPY®-LPS removal efficiency increased with increasing alkanediol chain length and the 1,2-alkanediol isomers were more effective than the terminal alkanediols at removing the BODIPY®-LPS. 1,2-hexanediol was the most efficient compound tested and out performed the detergent and alcohols. 1,2-butanediol and 1,6-hexanediol as well as 50% isopropanol and 75% ethanol reduced the BODIPY®-LPS associated with transferrin to similar levels. The removal of BODIPY®-LPS by the alkanediols was similar for both the transferrin and BSA complexes.

Reference to FIG. 2 illustrates BODIPY®-LPS Elution Profiles of BODIPY®-LPS-Transferrin Complexes on SP Sepharose® Fast Flow in Conjunction with Alkanediol Washes.

FIG. 3 illustrates the Reduction of BODIPY®-LPS from BODIPY®-LPS Transferrin Complexes in SP Sepharose® Fast Flow Eluates by Alkanediols. Chromatography was as described in FIG. 2. Zero percent reduction corresponds to a control run without an alkanediol wash. 1,1,2-hexanediol; 2, 1% Zwittergent® 3-14; 3,1,6-hexanediol; 4, ethylene glycol; and 5,1,4-butanediol. BODIPY®-LPS-transferrin complexes were generated, loaded onto a SP Sepharose® Fast Flow column and the resin washed with 50% solutions of 1,4-butanediol, 1,6-hexanediol, or 1,2-hexanediol. Following a wash to remove the alkanediol, transferrin was eluted as described in the methods. Sanitization between runs was with 0.5 N NaOH.

FIG. 4 illustrates the reduction of BODIPY®-LPS from BODIPY®-LPS-BSA complexes in SP Sepharose® Fast Flow eluates by alkanediols. Chromatography was as described in FIG. 2. Zero percent reduction corresponds to a control run without an alkanediol wash. 1,1,2-hexanediol; 2, 1% Zwittergent® 3-14; 3,1,2-butanediol; 4,1,6-hexanediol; 5, 50% isopropanol; 6, 75% ethanol; 7,1,4-butanediol; and 8, ethylene glycol.

It was noted during the experiments on transferrin utilizing 1,2-hexanediol in the wash that when the pH of the elution buffer was maintained at a pH of 5, including 1 M NaCl, that the transferrin was not eluted from the resin. Increased retention of transferrin was observed down to a 1,2-hexanediol concentration of 10%. At a 1,2-hexanediol concentration of 5%, transferrin retention was not altered. The alteration in retention times has been observed for other proteins during ion exchange chromatography in the presence of polyethylene glycol and other neutral polymers (Milby et al., 1989 and Gagnon et al., 1996). The changes in protein retention times were dependent on polyethylene glycol size and concentration and the protein itself. Whereas, ethylene glycol up to a concentration of 40% did not effect protein retention times (Tauc et al., 1998). It is worth while to note that in these instances the compound under investigation were included in all the chromatography buffers. For the 1,2-hexanediol, it was only included in a wash buffer that was then removed by an additional wash step prior to elution of the protein.

Since 1,2-hexanediol was the most effective compound tested for removing BODIPY®-LPS from both transferrin and BSA, the concentration dependence of the 1,2-hexanediol wash needed to affect this removal was investigated. The reduction of BODIPY®-LPS in the SP Sepharose® Fast Flow BSA eluate fraction was determined after 1,2-hexanediol washes containing 5%, 20%, and 50% 1,2-hexanediol. The 5% 1,2-hexanediol wash resulted in about a 55% decrease in the BSA associated BODIPY®-LPS while the reduction of BODIPY®-LPS by the 20% and 50% 1,2-hexanediol washes were comparable at approximately 96%.

In addition to transferrin and BSA, the removal of BODIPY®-LPS from lactoferrin complexes by 1,6-hexanediol was also examined by the fluorescent BODIPY® assay. The results of the analysis were then confirmed by analysis of the samples for the LPS marker compound 3-OH-14:0 fatty acids by GC-MS. Table V summarizes the data and again demonstrates the ability of an alkanediol, in this case 1,6-hexanediol, wash during the chromatography to reduce the levels of BODIPY®-LPS in the lactoferrin eluate. Approximately and 87% reduction of BODIPY®-LPS was observed by the BODIPY® fluorescence assay and a 91% reduction in the LPS marker by the GC-MS assay.

TABLE V

SPFF Chromatography Elution Profiles of BODIPY-LPS and BODIPY-LPS-Lactoferrin Complexes
BODIPY-LPS-lactoferrin complexes were generated, loaded onto a SP Sepharose Fast Flow column. For runs that include a 50% solution of 1,6-hexanediol, a wash to remove the 1,6-hexanediol was included prior to elution of lactoferrin as described in the methods. Column fractions were assayed for BODIPY and 3-OH-14:0 fatty acids as described in the methods.

| Sample | BODIPY-LPS (% Recovery) GCMS assay/Fluorescence BODIPY assay | | | |
|---|---|---|---|---|
|  | Load | Wash-unbound | Diol wash | Eluate |
| BODIPY-LPS | 100 (GCMS) | 94 | [1]N/A | 5 |
| (no diol wash) | 100 (fluor) | 89 | N/A | 7 |
| BODIPY-LPS-Lactoferrin | 100 | 62 | N/A | 48 |
| (no diol wash) | 100 | 60 | N/A | 46 |
| BODIPY-LPS-Lactoferrin | 100 | 63 | [2]ND | 4 |
| (+ diol wash) | 100 | 66 | 26 | 6 |

[1]N/A—Not applicable.
[2]ND—Could not be determined by GCMS.

Figure 5:
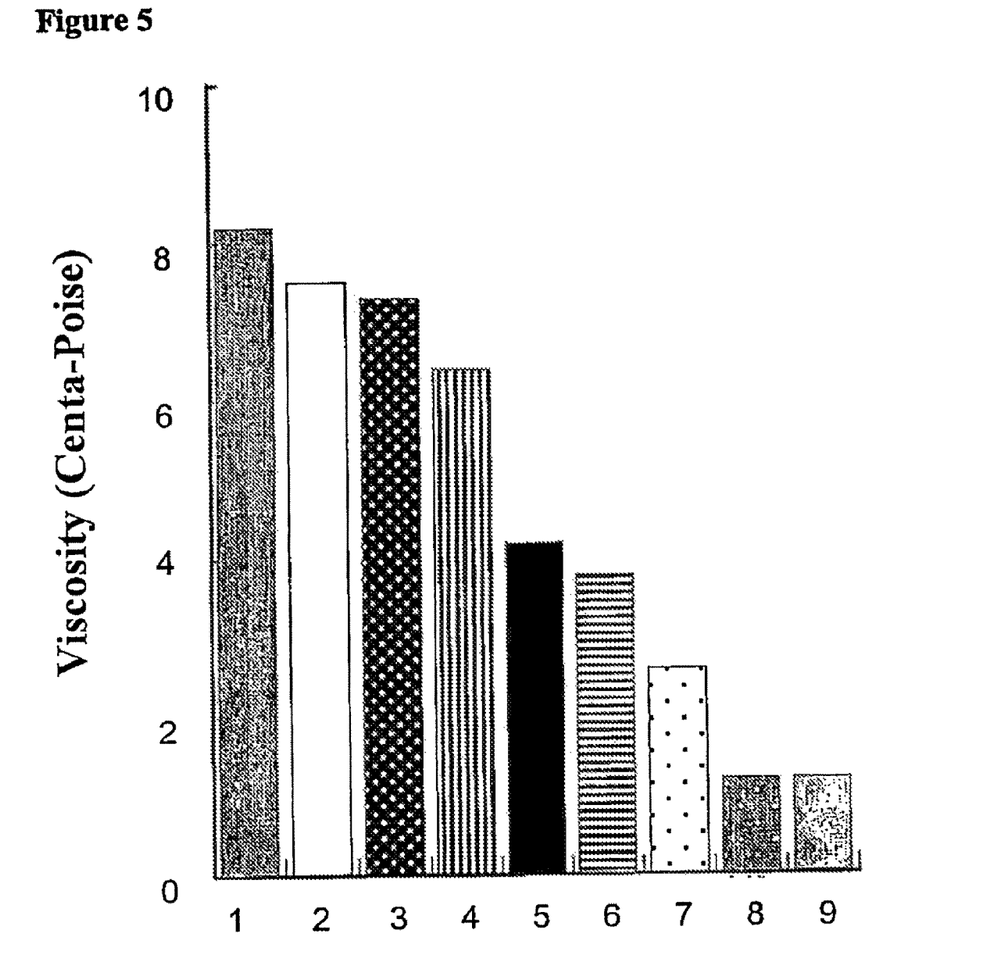
FIG. 5 is an illustration of viscosities of Alkanediol, Isopropanol, Ethanol, and Zwittergent® Solutions in 100 mM Acetate, pH 4.5. All solutions were prepared with 100 mM Acteate buffer, pH 4.5. 1, 50% 1,6-hexanediol; 2, 50% 1,2-hexanediol; 3, 50% 1,4-butanediol; 4, 50% 1,2-butanediol; 5, 50% Ethylene glycol; 6, 50% Isopropanol; 7, 75% Ethanol; 8, 1% Zw 3-14; and 9, 100 mM Acetate, pH 4.5.

During the chromatographic runs, a rise in the system back pressure was noted when the alkanediol washes were applied. The viscosity of each organic solutions and the Zwittergent® solution, prepared in 100 mM Acetate, pH 4.5, were measured (FIG. 5). The viscosity of the alkanediols increased with carbon chain length while the viscosity of the 1,2-alkanediol isomers were slightly less than the terminal alkanediol isomers. The increased viscosity of the alkanediol solutions may present some difficulties in scale-up. Column flow rates may have to be adjusted to maintain suitable system pressure for the equipment in use. Being able to use lower concentrations of the alkanediols to remove LPS from the protein-LPS complexes would partially alleviate this problem. For example, 20% and 50% 1,2-hexanediol to washes effectively reduce the BODIPY®-LPS to approximately the same levels for BSA complexes as indicated above. The viscosity of 20% 1,2-hexanediol is about one third that of 50% hexanediol, 2.6 Cp compared to 7.5 Cp.

Reduction of LPS from LPS-Protein Complexes by Alkanediols during Q Sepharose® Fast Flow Chromatography Removal of LPS from LPS-protein complexes is more complex on anion exchange resins, especially for basic proteins. During cation exchange chromatography, the LPS, being negatively charged, is not attracted to the functional group of the resin and is washed out of the column during the alkanediol wash while the protein remains bound under the wash conditions. During anion exchange chromatography, the LPS and the protein both are retained by the resin's functional groups. Therefore the complexes need to be disrupted and differential elution of the protein and LPS must occur.

The ability of 1,6-hexanediol and 1,2-hexanediol to reduce the BODIPY®-LPS levels of BSA-LPS complexes during anion exchange chromatography on Q Sepharose® Fast Flow resin was investigated. The two isomers, 1,2- and 1,6-, of hexanediol were chosen since these were the most effective compounds at reducing the levels of BODIPY®-LPS from protein complexes during cation exchange chromatography.

The elution of the BSA from the anion exchange resin after the application of a 1,2-hexanediol wash was altered as was observed for transferrin on the cation exchange resin. Increasing the salt concentration of the elution buffer to affect the elution of BSA after the 1,2-hexanediol wash resulted in the coelution of free BODIPY®-LPS with the BSA. An alternative elution scheme was chosen based on pH. After the 1,2-hexanediol wash was complete and a wash out of the 1,2-hexanediol had occurred, the BSA was eluted at pH 4.5. This was followed by a strip of the resin, which brought off the remaining BODIPY®-LPS, with a pH 4.5 buffer containing 1 M NaCl. Table VI summarizes the effect of 1,2-hexanediol on the removal of BODIPY®-LPS from BODIPY®-LPS-BSA complexes. Inclusion of the 1,2-hexanediol wash reduced the BODIPY®-LPS of the BSA eluate by about 29% with an apparent elution of the displaced BODIPY®-LPS to the 1,2-hexanediol wash fractions.

TABLE VI

The QFF Elution Profiles of BODIPY-LPS and BODIPY-LPS-BSA Complexes.

| | BODIPY-LPS (% Recovery) | | | | |
| --- | --- | --- | --- | --- | --- |
| Sample | Load | Wash-unbound | Diol wash | Elute | Strip |
| BODIPY-LPS [no diol wash] | 100 | 1 | NA | 0 | 42 |
| BODIPY-LPS-BSA [no diol wash] | 100 | 7 | NA | 17 | 52 |
| BODIPY-LPS-BSA [+diol wash] | 100 | 2 | 12 | 5 | 45 |

BODIPY-LPS and BODIPY-LPS-BSA complex were chromatographed on Q Sepharose Fast Flow. Column fractions were analyzed for BODIPY-LPS by the BODIPY assay as described in the methods.
[1]NA—Not applicable.

Alkanediol Effect on Enzymatic Activity

Lysozyme was used to determine the effect of the washing agents on enzymatic activity and thereby, indirectly the denaturing effects of the washing agents during SP Sepharose® Fast Flow chromatography. Lysozyme was chromatographed with and without a 6 CV %50 1,6-hexanediol wash or 1,2-hexanediol wash and the column loads and eluates assayed for lysozyme activity using a fluorescence microplate lysozyme activity assay. The hexanediol washes had no detrimental effects on lysozyme activity. 75% ethanol, 50% isopropanol, and 1% Zwittergent® 3-14 washes also had no effect on lysozyme activity.

What is claimed is:

1. A method of removing lipopolysaccharide from a recombinantly produced protein comprising a lipopolysaccharide-protein complex of lipopolysaccharide and protein comprising the steps of:
    (a) loading the recombinantly produced protein comprising the complex on to an ion exchange chromatographic resin;
    (b) washing the resin with an alkanediol wherein the lipopolysaccharide is separated from the complex and the protein is affixed to the resin; and
    (c) eluting the protein affixed to the resin to form an eluent such that the ratio of the protein to the lipopolysaccharide in the eluent is increased relative to the ratio of the protein to the lipopolysaccharide in the complex present in the recombinantly produced protein loaded on to the chromatographic resin in step (a).

2. The method of claim 1, wherein the alkanediol is selected from the group consisting of 1,5-pentanediol, 1,6-hexanediol, 1,2-hexanediol, 1,2-butanediol, 1,4-butanediol, and 1,7-heptanediol.

3. The method of claim 1, wherein the chromatographic resin is a cation exchange resin.

4. The method of claim 1, wherein the protein is selected from the group consisting of bovine albumin, bovine holotransferrin, lactoferrin, lysozyme, and heat shock proteins.

5. The method of claim 1, wherein greater than about 95% of the protein eluted from the chromatographic resin is free of the lipopolysaccharide.

6. The method of claim 5, wherein a change in pH or conductivity conditions applied to the chromatographic resin compared to pH or conductivity conditions employed to load the recombinantly produced protein comprising the complex on to the chromatographic resin is used to elute the protein from the chromatographic resin.

7. The method of claim 1, wherein the recombinantly produced protein is produced in a bacterial expression system.

8. The method of claim 7, wherein the bacterial expression system is selected from the group consisting of an *E. coli* expression system, a *Caulobacter crescent* expression system, and a *Proteus mirabilis* expression system.

9. The method of claim 2, wherein the alkanediol is 1,2-hexanediol.

10. The method of claim 9, wherein the protein is eluted by a change of pH conditions applied to the chromatographic resin compared to pH conditions employed to load the recombinantly produced protein comprising the complex on to the chromatographic resin.

11. A process of separating endotoxin from a protein-endotoxin complex comprising protein and endotoxin comprising the steps of:
    (a) affixing the protein-endotoxin complex to an ion exchange resin and
    (b) washing the resin with an alkanediol wherein the endotoxin is separated from the protein-endotoxin complex such that the ratio of the protein to the endotoxin in the protein-endotoxin complex is increased.

12. The process of claim 11, wherein the endotoxin is an impurity associated with the protein.

13. The process of claim 11, wherein greater than 99.9% of the endotoxin is separated from the protein-endotoxin complex.

14. A method of removing lipopolysaccharide from a recombinantly produced protein comprising a lipopolysaccharide-protein complex of lipopolysaccharide and protein comprising the steps of:
(a) affixing the recombinantly produced protein comprising the complex to a cation exchange chromatographic resin under a first pH and/or first conductivity condition;
(b) washing the cation exchange chromatographic resin with an alkanediol wherein the lipopolysaccharide is separated from the complex such that the ratio of the protein to the lipopolysaccharide in the recombinantly produced protein is increased and
(c) eluting the protein from the cation exchange chromatographic resin by either changing the pH or the conductivity relative to the first pH and/or the first conductivity condition.

15. A method of removing lipopolysaccharide from a recombinantly produced protein comprising a lipopolysaccharide-protein complex of lipopolysaccharide and protein comprising the steps of:
(a) loading the recombinantly produced protein comprising the complex to an anion exchange resin;
(b) affixing the lipopolysaccharide to the anion exchange resin and
(c) washing the anion exchange resin with an alkanediol and
(d) eluting the lipopolysaccharide from the resin such that the ratio of the protein to the lipopolysaccharide in the lipopolysaccharide-protein complex is increased.

* * * * *